US00PP23401P2

(12) United States Plant Patent
Pullen et al.

(10) Patent No.: US PP23,401 P2
(45) Date of Patent: Feb. 19, 2013

(54) STRAWBERRY PLANT NAMED 'DRISSTRAWTWENTYTHREE'

(50) Latin Name: *Fragaria×ananassa*
Varietal Denomination: DrisStrawTwentyThree

(75) Inventors: Esther J. Pullen, Valrico, FL (US); Philip J. Stewart, Watsonville, CA (US); Kristie L. Gilford, Dover, FL (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/200,894

(22) Filed: Oct. 4, 2011

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawTwentyThree' characterized by having very large, bi-conical fruit with medium sweetness and high yield is disclosed.

3 Drawing Sheets

Genus and species: *Fragaria×ananassa.*
Variety denomination: 'DrisStrawTwentyThree'.

BACKGROUND OF THE NEW PLANT

The present invention relates to a new and distinct strawberry variety designated 'DrisStrawTwentyThree' and botanically known as *Fragaria×ananassa*. This new strawberry variety was discovered in Hillsborough County, Fla. in December 2007 and originated from a cross between the proprietary female parent '1M16' (unpatented) and the proprietary male parent '87K286' (unpatented). A single plant was selected for asexual propagation via tissue culture and vegetative cuttings in Shasta County, Calif. in 2007.

'DrisStrawTwentyThree' underwent further testing in Hillsborough County, Fla. for five years (2007-2011). The present invention has been found to retain its distinctive characteristics through successive asexual propagations via stolons.

Plant Breeder's Rights for this variety have not been applied for. 'DrisStrawTwentyThree' has not been made publicly available or sold more than one year prior to the filing date of this application.

SUMMARY OF THE INVENTION

The following are the most outstanding and distinguishing characteristics of this new cultivar when grown under normal horticultural practices in Hillsborough County, Fla.

1. High yield;
2. Very large, bi-conic shaped fruit; and
3. Medium sweetness.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
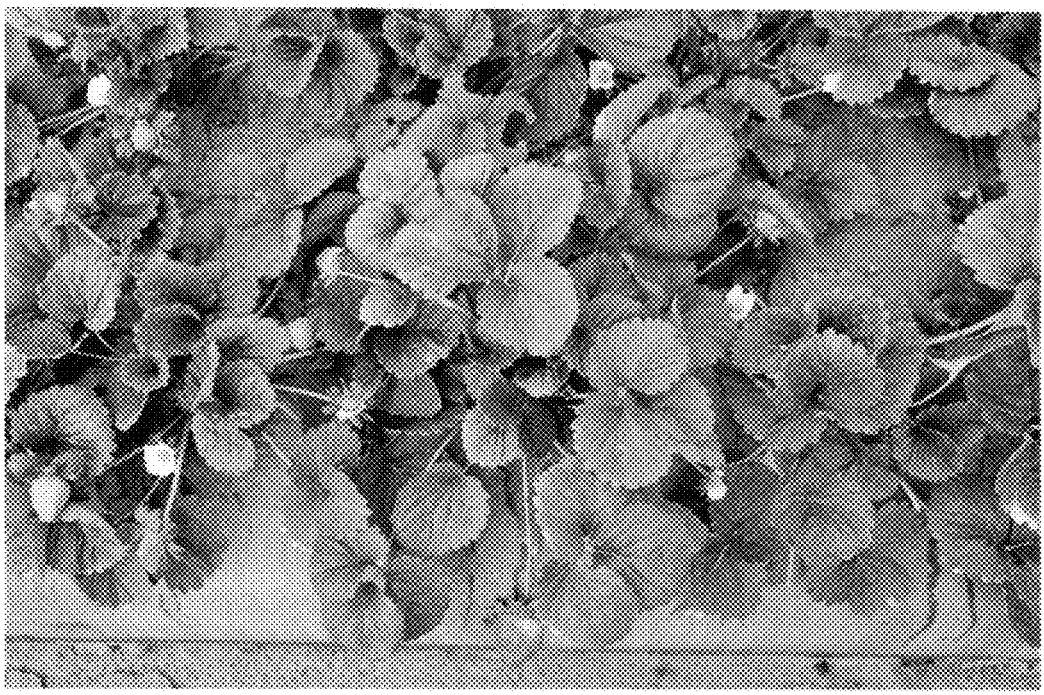
FIG. 1 shows overall plant habit including fruit at various stages of development.
Figure 2:
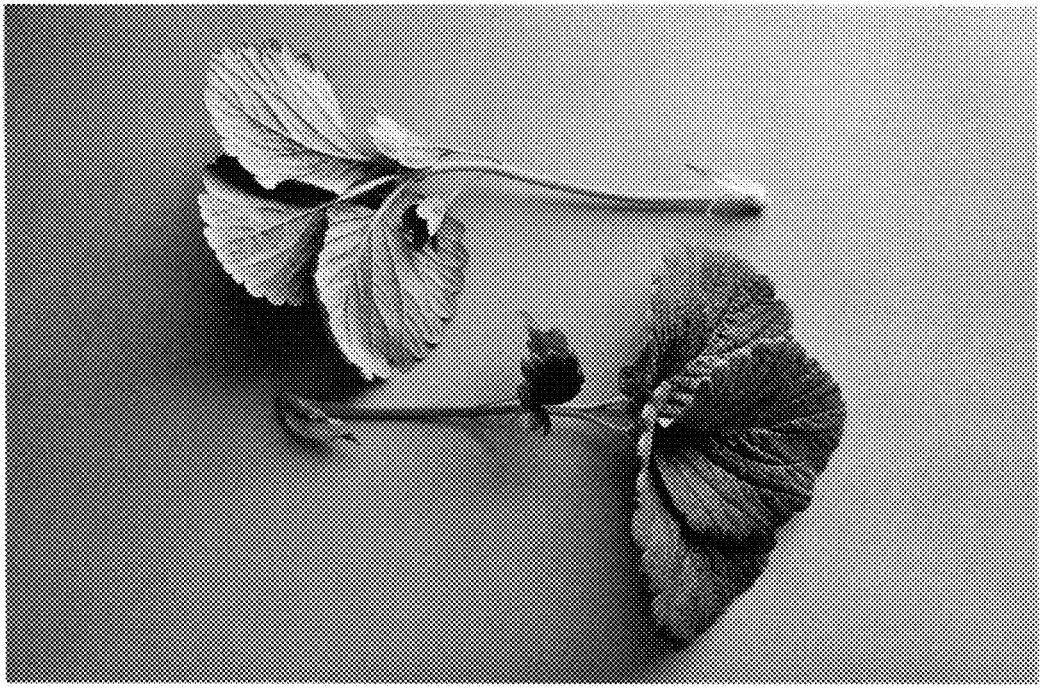
FIG. 2 shows upper and lower surfaces of the leaves of the plant with three leaflets.
Figure 3:
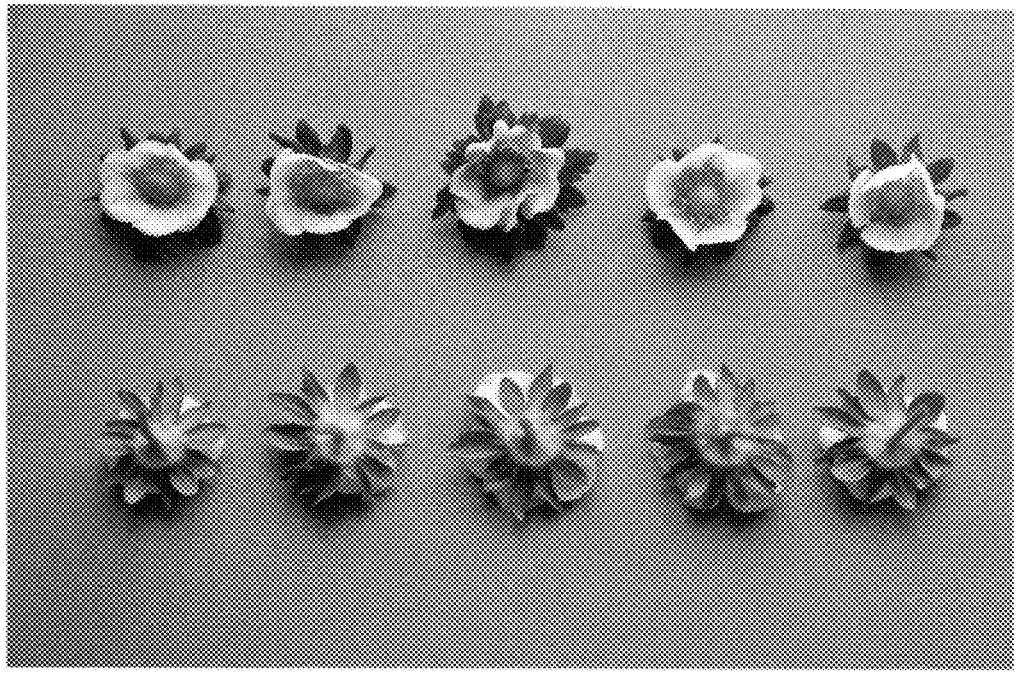
FIG. 3 shows both upper and lower surfaces of the flowers.
Figure 4:
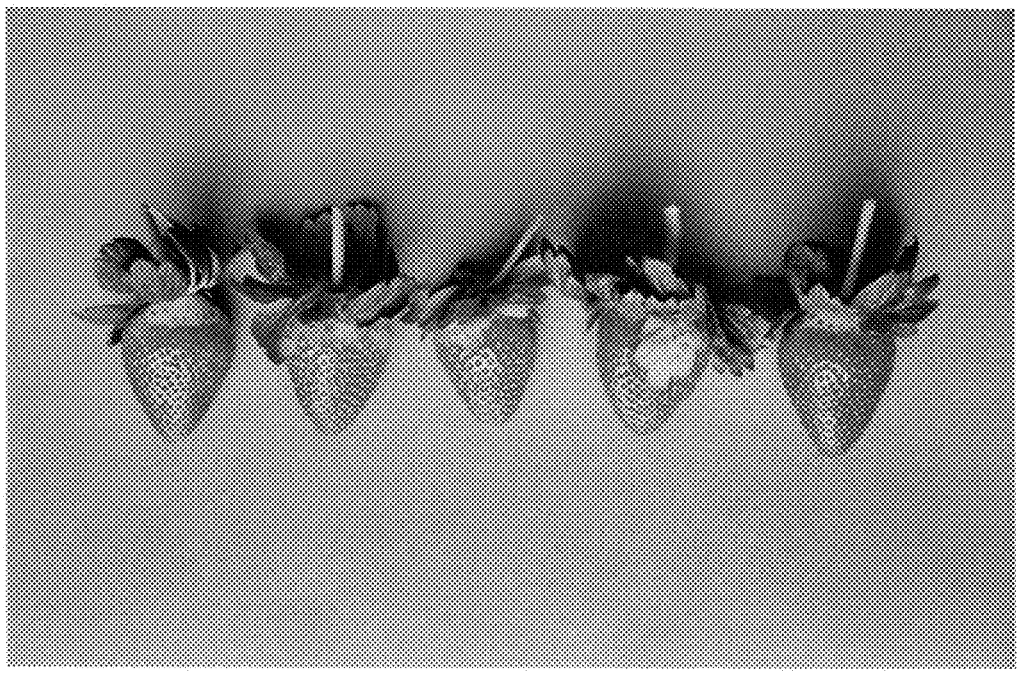
FIG. 4 shows the whole fruit.
Figure 5:
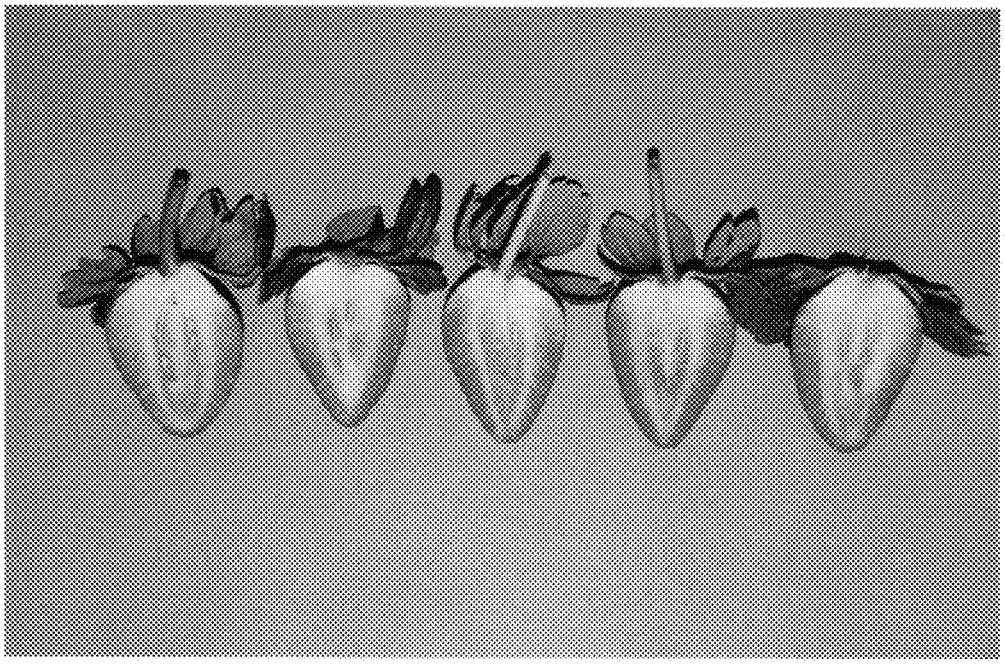
FIG. 5 shows the fruit in longitudinal cross-section.

The following detailed descriptions set forth the distinctive characteristics of 'DrisStrawTwentyThree'. The data which define these characteristics is based on observations taken in Hillsborough County, Fla. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentyThree' has not been observed under all possible environmental conditions. The botanical description of 'DrisStrawTwentyThree' was taken from four-month-old plants. Color terminology follows The Royal Horticultural Society Colour Chart, London (R.H.S.) (2001 edition). Descriptive terminology follows the *Plant Identification Terminology, An Illustrated Glossary*, 2$^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawTwentyThree'.

Parentage:

*Female parent.*—The proprietary variety '1M16' (unpatented).
*Male parent.*—The proprietary variety '87K286' (unpatented).

Plant:
*Height*.—24.7 cm.
*Diameter*.—45.5 cm.
*Number of crowns/plant*.—3.
*Habit*.—Upright in center of plant; Flat — spreading at outside of plant.
*Density of individual plant*.—Dense at center of plant; Open — sparse at outside of plant.
*Vigor* (*health and hardiness of plant*).—Medium — strong.

Terminal leaflets:
*Size*.—Medium. Length: 8.1 cm. Width: 8.3 cm. Length/width ratio: 1.0 (As long as broad).
*Number of teeth/terminal leaflet*.—23.
*Shape of teeth*.—Rounded — crenate.
*Color*.—Upper surface: RHS 139A (Dark green). Lower surface: RHS 148B (Medium yellow-green).
*Shape in cross section*.—Concave.
*Blistering*.—Medium.
*Glossiness*.—Medium.
*Number of leaflets*.—Three only.
*Shape*.—Orbicular.
*Base shape*.—Rounded.
*Apex descriptor*.—Rounded.
*Variegation*.—Absent.
*Margin*.—Crenate.
*Margin profile*.—Revolute (margins rolled backwards).

Petiole:
*Length*.—12.7 cm.
*Diameter*.—3.71 mm.
*Pubescence*.—Sparse.
*Pose of hairs*.—Outwards-horizontal.
*Color*.—RHS 151A (Medium yellow-green).

Petiolule:
*Length*.—14.61 mm.
*Diameter*.—1.85 mm.
*Bract frequency*.—2.
*Color*.—RHS 151A (Medium yellow-green).

Stipule:
*Length*.—3.6 cm.
*Width*.—10.79 mm.
*Pubescence*.—Medium.
*Anthocyanin coloration*.—Absent or very weak.

Stolon:
*Number*.—Absent or very few.
*Average number of daughter plants per plant*.—68.
*Anthocyanin coloration*.—Absent or very weak; RHS 4B (Medium yellow).
*Thickness*.—Medium.
*Pubescence*.—Medium.

Inflorescence:
*Position relative to foliage*.—Beneath.
*Number of flowers*.—Medium.
*Time of flowering* (50% *of plants at first flower*).—Early.
*Flower size*.—Medium.
*Flower diameter*.—32.60 mm.
*Petals*.—Shape: Orbicular. Apex: Rounded. Base: Concavo-convex. Margin: Entire. Spacing: Overlapping. Length: 16.10 mm. Width: 15.42 mm. Length/width ratio: As long as broad; 1.0. Typical and observed petal number per flower: 6. Color (upper surface): RHS 155B (White).
*Calyx*.—Diameter: 40.44 mm. Diameter relative to corolla: Larger. Inner calyx diameter relative to outer: Same size. Insertion of calyx: Set above fruit — raised. Pose of calyx segments: All poses are present. Size of calyx in relation to fruit: Much smaller. Adherence of calyx: Very strong.
*Sepal*.—Shape: Elliptical. Apex: Truncate. Margin: Entire. Length: 13.26 mm. Width: 7.13 mm. Typical and observed sepal number per flower: 13.
*Receptacle color*.—RHS 151A (Medium yellow-green).
*Stamen*.—Present. Anther color: RHS 153D (Medium yellow-green).
*Pedicel*.—Attitude of hairs: Upwards.

Fruiting truss:
*Length*.—Medium; 16.5 cm.
*Diameter at base of truss*.—3.49 mm.
*Number of berries per fruiting truss*.—1.
*Attitude at first picking*.—Prostrate.
*Color at base of truss*.—RHS 144B (Medium yellow-green).

Fruit:
*Relative fruit size*.—Very large.
*Length*.—57.84 mm.
*Width*.—43.01 mm.
*Length/width ratio*.—1.3 (Longer than broad).
*Fruit hollow length*.—43.74 mm.
*Fruit hollow width*.—12.84 mm.
*Fruit hollow length/width ratio*.—3.4.
*Fruit hollow center* (*cavity*).—Very large.
*Weight* (*per individual berry*).—29.2 g.
*Predominant fruit shape*.—Bi-conical.
*Difference in shape between primary and secondary fruits*.—None or very slight.
*Evenness of fruit surface*.—Even or very slightly uneven.
*Fruit skin color*.—RHS N34A (Dark orange-red).
*Evenness of fruit color*.—Slightly uneven.
*Fruit glossiness*.—Medium.
*Achenes*.—Insertion of achenes: Above surface. Coloration (sunward side of berry): RHS 172A (Dark greyed-orange). Coloration (shaded side of berry): RHS 163C (Medium greyed-orange). Number per berry: 280. Weight (weight achenes divided by total # seed): 0.0005712701. Width of band without achenes: Very broad.
*Firmness of flesh*.—Medium.
*Color of flesh* (*excluding core*).—RHS 42B (Medium red) and RHS 155B (White).
*Color of core*.—RHS 39A (Medium red) and RHS 155D (White).
*Evenness of flesh color*.—Slightly uneven.
*Distribution of flesh color*.—Marginal and central.
*Sweetness*.—Medium.
*Acidity*.—Medium.
*Texture when tasted*.—Coarse.
*Type of bearing*.—Not everbearing — not remontant.
*Grams of fruit/plant*.—616.3 g.
*Harvest interval*.—Late November — early April.
*Harvest maturity*.—Early.

Disease, pest, and stress resistance:
*Botrytis fruit rot*.—Moderately susceptible.
*Powdery mildew*.—Moderately susceptible.
*Verticillium wilt*.—Moderately susceptible.
*Xanthomonas fragariae*.—Susceptible.
*High temperatures*.—Moderately resistant.
*High pH*.—Moderately resistant.
*Cold temperatures*.—Susceptible.

COMPARISON WITH PARENTAL AND COMMERCIAL VARIETIES

When 'DrisStrawTwentyThree' is compared to the proprietary female parent '1M16' (unpatented), 'DrisStrawTwentyThree' has higher yields and larger fruit than '1M16'.

When 'DrisStrawTwentyThree' is compared to the proprietary male parent '87K286' (unpatented), 'DrisStrawTwentyThree' has much higher yields than. '87K286'.

When 'DrisStrawTwentyThree' is compared to the commercial variety 'Driscoll Sanibel' (U.S. Plant Pat. No. 16,298), 'DrisStrawTwentyThree' has a revolute terminal leaflet margin profile, a rounded terminal leaflet base, and stolons with absent or very weak anthocyanin coloration, while 'Driscoll Sanibel' has a flat terminal leaflet margin profile, an obtuse terminal leaflet base, and stolons with strong anthocyanin coloration. Additionally, 'DrisStrawTwentyThree' has bi-conical shaped fruit with a very broad band without achenes and a coarse texture on a plant that is not everbearing, while 'Driscoll Sanibel' has conical shaped fruit with a narrow band without achenes and a fine texture on a plant that is partially everbearing.

We claim:

1. A new and distinct variety of strawberry plant named 'DrisStrawTwentyThree' as described and shown herein.

* * * * *